(12) United States Patent
Zhou et al.

(10) Patent No.: US 9,205,175 B2
(45) Date of Patent: Dec. 8, 2015

(54) THERMOSENSITIVE AND CROSSLINKABLE POLYMER COMPOSITE FOR THREE-DIMENSIONAL SOFT TISSUE SCAFFOLD PRINTING

(71) Applicants: Gongyao Zhou, Wilmington, DE (US); Christopher Geisler, Newtown, PA (US)

(72) Inventors: Gongyao Zhou, Wilmington, DE (US); Christopher Geisler, Newtown, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 13/951,936

(22) Filed: Jul. 26, 2013

(65) Prior Publication Data

US 2014/0179822 A1    Jun. 26, 2014

Related U.S. Application Data

(60) Provisional application No. 61/676,466, filed on Jul. 27, 2012.

(51) Int. Cl.
| | | |
|---|---|---|
| *C08L 53/00* | (2006.01) | |
| *A61L 27/52* | (2006.01) | |
| *A61L 27/26* | (2006.01) | |
| *A61L 27/48* | (2006.01) | |

(52) U.S. Cl.
CPC .............. *A61L 27/52* (2013.01); *A61L 27/26* (2013.01); *A61L 27/48* (2013.01); *C08L 53/00* (2013.01); *A61L 2430/34* (2013.01)

(58) Field of Classification Search
USPC ............................................. 525/89
See application file for complete search history.

(56) References Cited

U.S. PATENT DOCUMENTS

| | | |
|---|---|---|
| 6,410,645 B1 | 6/2002 | Pathak et al. |
| 7,192,693 B2 | 3/2007 | Bryant et al. |
| 8,197,743 B2 | 6/2012 | Wicker et al. |
| 8,383,586 B2 | 2/2013 | McKay et al. |
| 2004/0137225 A1* | 7/2004 | Balkus et al. ................. 428/364 |
| 2006/0018948 A1 | 1/2006 | Guire et al. |
| 2007/0207094 A1* | 9/2007 | Oxman et al. ................. 424/49 |
| 2009/0258051 A1* | 10/2009 | Chidambaram et al. ...... 424/423 |
| 2011/0097406 A1 | 4/2011 | Bryant et al. |

FOREIGN PATENT DOCUMENTS

WO     WO2010/043892     4/2010

OTHER PUBLICATIONS

Ward, Mark A. et al, "Thermoresponsive Polymers for Biomedical Applications", Polymers, Aug. 3, 2011, pp. 1215-1242.

Tsang, Valerie Liu et al., "Three-dimensional tissue fabrication", Advanced Drug Delivery Reviews, Jul. 19, 2004, pp. 1635-1647.

* cited by examiner

*Primary Examiner* — Jeffrey Mullis
(74) *Attorney, Agent, or Firm* — Joseph E. Maenner; Maenner & Associates, LLC

(57) ABSTRACT

A hydrogel material for use in three-dimensional scaffold printing is disclosed. The material is formed from a first triblock polymer having a formula ABA and a second triblock polymer having a formula AmaBAma, wherein A is a first polymer, B is a second polymer, and Ama is a methacrylate of the first polymer. The material is thermosensitive and photo-crosslinkable. A method of manufacturing the material is also disclosed.

15 Claims, 7 Drawing Sheets

| Mix of PEG-PLGA-PEG and PEGma-PLGA-PEGma (550-2810-550/526-2810-526) with 0.03% Irgacure 2959 ||||||
|---|---|---|---|---|---|
| Mix Ratio | Solution Minimum Viscosity (cP) | Material Maximum Viscosity (cP) | Maximum Viscosity Temperature (°C) | Maximum Elastic Modulus (Pa) | Maximum Elastic Modulus Temperature (°C) |
| 50/50 | 64 | 76,790 | 33.7 | 34.3 | 35.75 |
| 35/65 | 217.75 | 81,510 | 37 | 63.745 | 40 |
| 20/80 | 228.435 | 122,836.10 | 33.3 | 93.888 | 33.98 |
| 10/90 | 12.39 | 50,210 | 75 | 7.701 | 75 |

THERMOSENSITIVE AND CROSSLINKABLE POLYMER COMPOSITE FOR THREE-DIMENSIONAL SOFT TISSUE SCAFFOLD PRINTING

CROSS-REFERENCE TO RELATED APPLICATION

This application claims the benefit of the filing date of U.S. provisional application No. 61/676,466, filed on Jul. 27, 2012, the teachings of which are incorporated herein by reference.

STATEMENT REGARDING FEDERALLY SPONSORED RESEARCH OR DEVELOPMENT

This invention was made with government support under Contract No. CMMI-0700139 awarded by the National Science Foundation. The government has certain rights in the invention.

BACKGROUND OF THE INVENTION

1. Field of the Invention

The present invention relates to a thermosensitive and photocrosslinkable composite material that may be used in three-dimensional scaffold printing.

2. Description of the Related Art

In the US alone, around eight million surgical procedures are performed every year to treat maladies related to damaged tissue; over 70,000 patients are waiting for organ transplants, and more than 100,000 people die each year with tissue related disorders. The current demands for replacement organs and tissues far exceed the supply, and research indicates that this gap will continue to widen. The history of reconstructive surgery began with ablative surgery, followed by tissue and organ transplantation, leading to contemporary tissue reconstruction. In recent years, the main focus of tissue engineering has been on the culture of cells. In general, tissues are three-dimensional ("3-D") structures composed of living cells and a support structure. Therefore, the generation of functional implants from living cells relies heavily on the fabrication of the 3-D structure. Tissue engineering has been successfully used to replace skin, blood vessels, and cardiac tissue. For a new generation of complex 3-D implants, more sophisticated technology is required. Complex shapes and structures can be created from special biodegradable and biocompatible polymers so that a tissue's natural support structure replaces the synthetic scaffold as it degrades. The materials should therefore be considered only as a temporary support for cell growth and cell adhesion. For engineering soft tissues, ideal scaffolds are made of synthetic or natural biopolymers providing porous (up to 90%) support structure, thus mimicking the natural extracellular matrix environment in which cells attach, multiply, migrate and function. The pores in the scaffold must be interconnected to allow efficient nutrient transfer and waste exchange to permit survival of any cells cultured on the scaffold. The pores should typically be 100-300 μm, around 5-10 times a cell's diameter. Porous scaffolds facilitate tissue formation while providing adequate mechanical strength to withstand implantation and permit normal physiological function in the human body.

There exists a need for a temporary scaffolding material that is thermoresponsive and photocrosslinkable as well as designed and fabricated to be used in many different applications of solid freeform fabrication.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a hydrogel material for use in three-dimensional scaffold printing is disclosed. The material is formed from a first triblock polymer having a formula ABA and a second triblock polymer having a formula AmaBAma, wherein A is a first polymer, B is a second polymer, and Ama is a methacrylate of the first polymer. The material is thermosensitive and photocrosslinkable.

In another embodiment, the present invention is a method of forming a hydrogel material comprising the steps of: providing a first triblock polymer having a formula ABA; blending a second triblock polymer having a formula AmaBAma with the first triblock polymer, forming a blend, wherein A is a first polymer, B is a second polymer, and Ama is a methacrylate of the first polymer; and heating the blend to between about 33 degrees Celsius and about 34 degrees Celsius.

BRIEF DESCRIPTION OF THE DRAWINGS

Other aspects, features, and advantages of the present invention will become more fully apparent from the following detailed description, the appended claims, and the accompanying drawings in which like reference numerals identify similar or identical elements.

DETAILED DESCRIPTION

Figure 1:
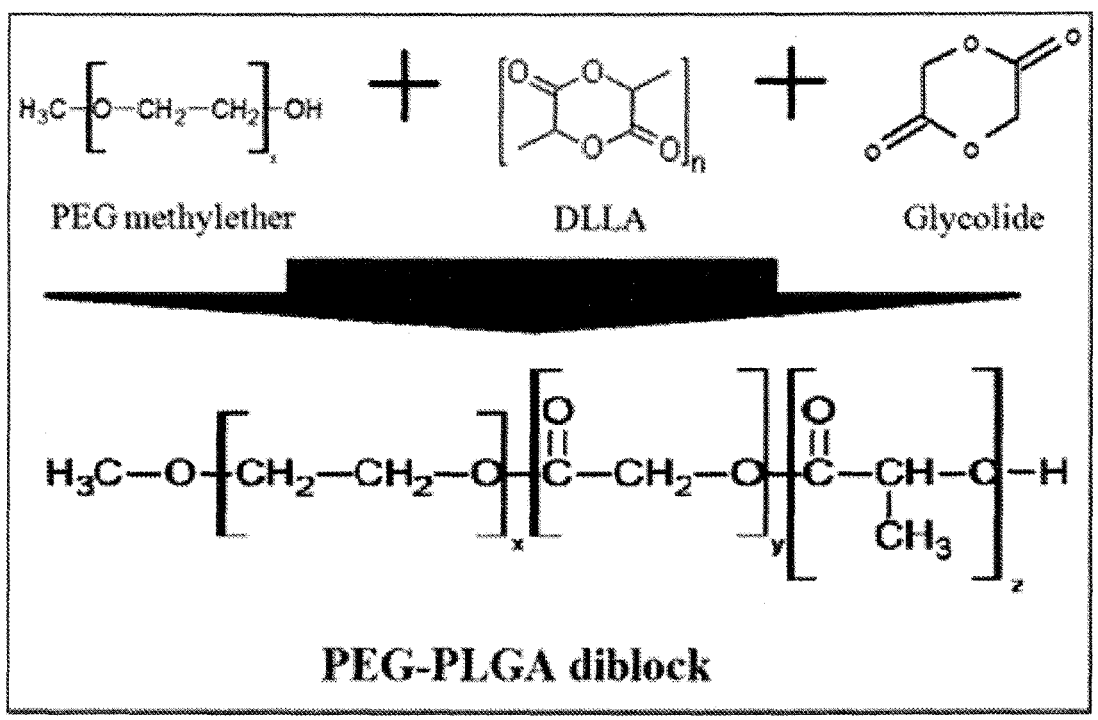
FIG. 1 shows the chemical formation of a PEG-PLGA diblock polymer.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Hydrogels have been widely used in various biomedical applications, including tissue engineering, due to their biocompatibility, low toxicity and low cost. Hydrogels are hydrophilic polymer networks that can absorb up to a thousand times their dry weight in water. Their high water contents make them more similar to native tissues than dry porous polymer scaffolds. Hydrogels can either be chemically stable or degradable which eventually disintegrate and dissolve. Hydrogels are called 'physical' gels when the networks are held together by molecular entanglements and/or secondary forces including ionic, hydrogen-bonding or hydrophobic forces. Physical hydrogels are not homogeneous, since clusters of molecular entanglements, or hydrophobically- or ionically-associated domains, can create inhomogeneities. Free chain ends or chain loops also represent transient network defects in physical gels. The polymer chains can be easily modified to vary the resultant hydrogel properties to fit the application. For tissue engineering ("TE") purposes, hydrogels may be functionalized to promote cell proliferation, migration and adhesion. In addition, hydrogels are highly permeable, which facilitates exchange of oxygen, nutrients, and other water soluble metabolites, making them ideal for cell encapsulation. The hydrophilicity inhibits protein adsorption, thereby minimizing the foreign body responses when implanted in vivo.

A novel material has been developed that is capable of being used in numerous types of solid freeform fabrication ("SFF") printers to print 3-dimensional scaffolds for soft tissue. A 20/80 mix of low molecular weight poly(ethylene glycol-b-(DL-lactic acid-co-glycolic acid)-b-ethylene glycol) PEG-PLGA-PEG and low molecular weight PEGma-PLGA-PEGma triblock copolymer dissolved with Irgacure® 2959 (manufactured by CIBA®) in de-ionized ("DI") water produced a material that is of low viscosity to allow for easy movement through SFF printers. This biocompatible and degradable material possesses a two stage gelation process. It is a non-viscous 228 centipoise ("cP") solution at 20° C. and quickly transitions to a more 122,836 cP viscous material with an increase in temperature to 33° C. To increase the material properties further and create a network of irreversible crosslinks, irradiation of UV light is used. This material accomplishes all necessary requirements for it to be applicable for SFF printers: 1) low viscous solution before printing, 2) no mixing is needed to form a homogenous gel, 3) has a short solution to gel transition time, 4) mechanically strong material to allow for vertical building, and 5) irreversible gel to prevent deformation of the final printed structure.

A photocrosslinkable material permits quick gelation and eliminated the need for multiple print heads since it does not need another crosslinking material. The challenges with photocrosslinkable material was the UV light irradiation source and the ability of a droplet of material to hold its shape after printing before gelation. Thermosensitive materials were able to gel rapidly allowing for material to hold its shape after printing but, unlike photocrosslinkable material, was reversible. To be able to create a thermosensitive material with the mechanical properties to allow for 3-dimensional building, a high viscous initial material was needed after printing and before irradiation. The combination of thermosensitive and photocrosslinkable material met every need for SFF printing.

Figure 3:
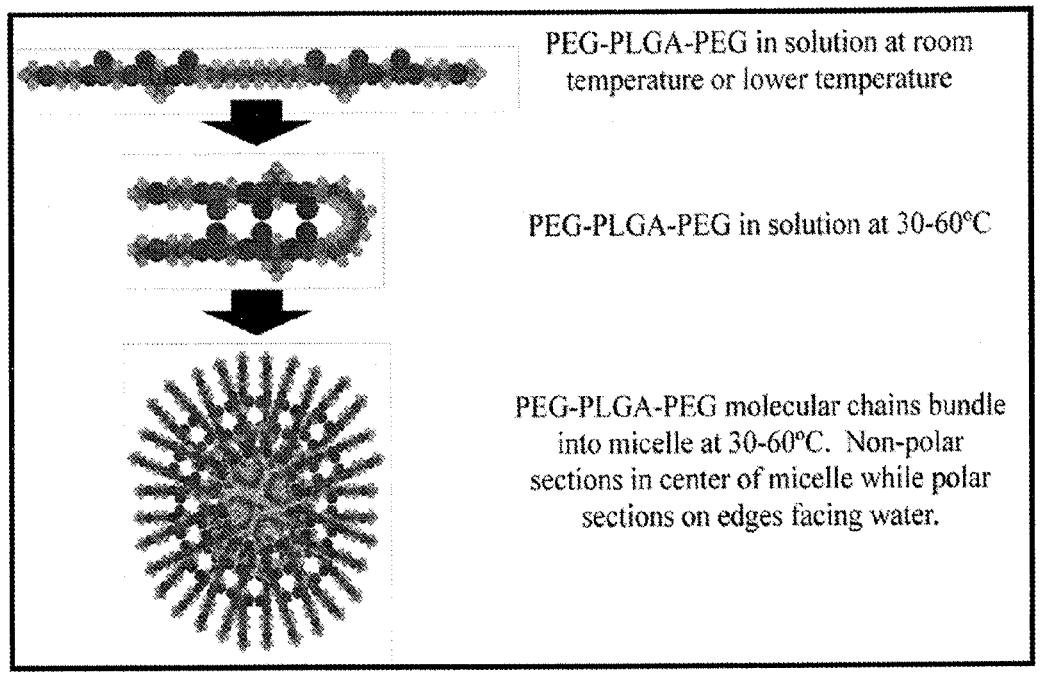
FIG. 3 shows the formation of a PEG-PLGA-PEG micelle.
Figure 4:
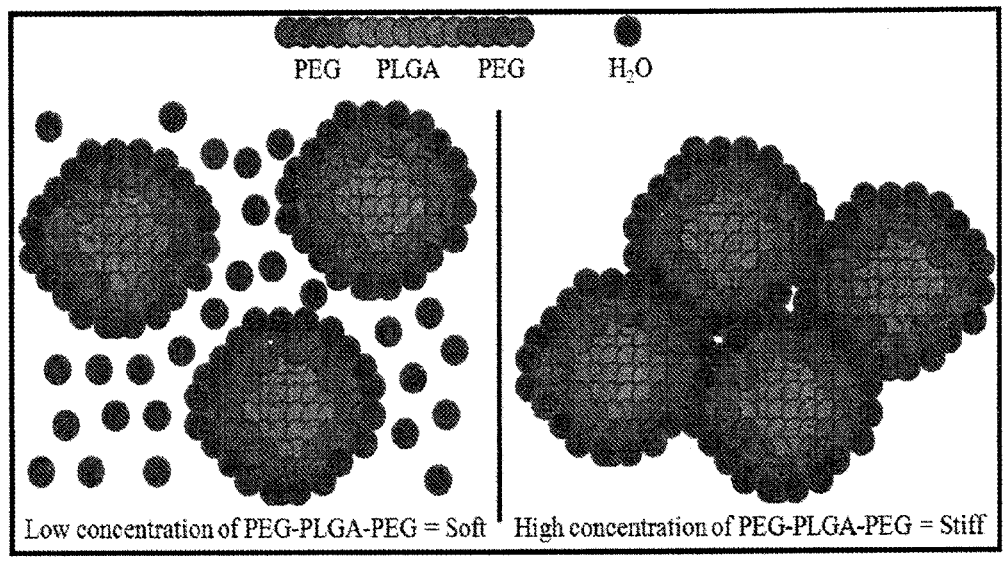
FIG. 4 shows the concentration of the PEG-PLGA-PEG micelle in water.

A thermosensitive material, PEG-PLGA-PEG, was examined as well as the mechanism of gelation and the effect of altering the molecular weights of the PEG and PLGA. PEG-PLGA-PEG, dissolved in water, becomes a gel as temperature increases past its sol-to-gel transition point because of the formation of micelles in the material. PLGA is hydrophobic and is the driving force of micelle formation. As temperature increases, the PLGA parts of the copolymer chains clump together with the PEG compounds interacting with the water because of its hydrophilicity. The micelles continue to grow as temperature increases. The formation of micelles is shown in FIG. 3. The concentration of PEG-PLGA-PEG determines the stiffness of the resulting structure, as exemplified in FIG. 4.

To help increase the mechanical properties and long term stability of the gel, Irgacure 2959, a photoinitiator, was added to the triblock. Irgacure 2959 works by breaking double bonds between carbon molecules, stabilizing that bond, and then repeating. Irgacure 2959 breaks apart into free radicals once it is initiated by UV light irradiation. The free radicals are what break apart the carbon double bonds because they are less stable than single carbon bonds. The radicals start a chain reaction of breaking apart carbon double bonds and securing other available free carbons to form a network of crosslinks. PEG-PLGA-PEG does not have any available carbon double bonds for Irgacure to break so a different type of PEG was needed since the PEG was the outside component of the triblock with an available free end. PEG methacrylate was substituted for the original PEG methyl ether.

A material that was a combination of PEG-PLGA-PEG and PEGma-PLGA-PEGma with Irgacure 2959 gelled thermally and possessed the ability to crosslink with UV light. Four different types of mixes of PEG-PLGA-PEG/PEGma-PLGA-PEGma were prepared and compared: 50/50, 35/65, 20/80, and 10/90. A final polymer concentration of 45% in water was used since this percentage consistently had the best material properties as shown in previous tests. As the ratio increased from 50/50 to 20/80, the material became more viscous thermally and stiffer as a UV crosslinked material. Above 20/80, the 10/90 material's properties declined and looked similar to the properties of PEGma-PLGA-PEGma material. The 20/80 mix was found to have the highest maximum viscosity of 122,836 cP, which is comparable to sour cream and peanut butter, and also have the highest elastic modulus. The elastic modulus was reached at the lowest temperature, helping to prevent evaporation of the water content. After micelle formation, the 50/50, 35/65, and 20/80 mixes of materials are able to hold its shape allowing for UV irradiation to create permanent crosslink and increase the mechanical properties of the material. The 20/80 mix had the highest solution viscosity, 228 cP, but the value is still within the range of viscosity that most SFF printers are capable of handling. The 20/80 mix also had the highest elastic modulus as a gel, 93.9 Pascals (Pa), of all materials tested. Thermally, the material did not technically form a gel since the elastic modulus was never greater than the viscous modulus but the material was stiff enough to be able to hold its shape before UV irradiation. This material retained the best photosensitivity of all mixed triblock polymer materials; it gelled the quickest and was able to hold its shape and even hold a shape it was molded into.

A 20/80 mix of low molecular weight PEG-PLGA-PEG and low molecular weight PEGma-PLGA-PEGma mixed with Irgacure 2959 gelled with the help of temperature and UV irradiation and is capable of 3-D building. This material mixed with de-ionized water forms a material that has low viscosity as a solution at low temperature and is capable of drastically increasing viscosity and mechanical properties at a temperature of about 33° C. This material is capable of holding its 3-D shape in order for UV irradiation to further increase the mechanical properties and form an irreversible network of crosslinks to confirm that the structure of the material will be permanent before degradation of the materials occur.

In an exemplary embodiment, a hydrogel material according to the present invention is composed of a blend of a first triblock polymer having a formula ABA and a second triblock polymer having a formula AmaBAma. A is a first polymer, B is a second polymer, and Ama is a methacrylate ("ma") of the first polymer. In a further exemplary embodiment, A is hydrophilic material, such as polyethylene glycol (PEG), and B is a hydrophobic material, such as poly(DL-lactic acid-co-glycolic acid) (PLGA), such that ABA has a specific formula PEG-PLGA-PEG and AmaBAma has a specific formula PEGma-PLGA-PEGma.

The exemplary blend comprises about 20 percent by weight of PEG-PLGA-PEG and about 80 percent by weight of PEGma-PLGA-PEGma. The PEG has a molecular weight of about 550 and the PLGA has a molecular weight of about 2810, such that the PLGA has a molecular weight about 5.1 times the molecular weight of the PEG. Additionally, the PEGma has a molecular weight of about 526 such that the PLGA has a molecular weight about 5.3 times the molecular weight of the PEGma.

To synthesis the PEG-PLGA-PEG polymer, polyethylene glycol (PEG) methyl ether (Mn=550, 750, and 1,000 g/mol), DL-lactide (DLLA), glycolide (GA), anhydrous toluene, and hexamethylene diisocynate (HMDI) were all used. All solvents and other chemicals are of analytical grade.

PEG is typically terminated with hydroxyl groups which can serve as a point of synthetic modification. The free hydroxyl groups of PEG are ring-opening initiators for lactide and glycolide. Lactide and glycolide in the molar ratio of 78/22 were used to create a PLGA material of molecular number 1405. Ring opening polymerization of lactide and glycolide onto monomethoxypoly(ethylene glycol), molecular weight of 550, using stannous octoate (tin(II) 2-ethylhexanoate) (SnOct) as the catalyst was performed to synthesize PEG-PLGA diblock copolymers, shown in FIG. 1.

Figure 2:
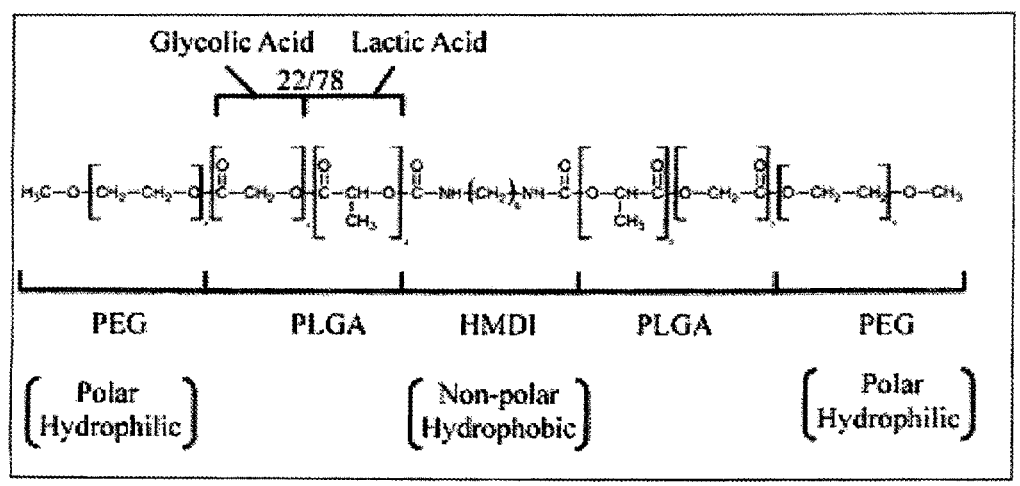
FIG. 2 shows the chemical formula of a PEG-PLGA-PEG triblock polymer.

In ring opening polymerization, the terminal end of the polymer, the hydroxyl end group (—OH) of the PEG, acts as a reactor and breaks apart a cyclic monomer, Glycolide and DLLA, to form a large polymer chain. The polymer chain that is formed is the diblock polymer PEG-PLGA. Anhydrous toluene was added as a solvent in the reaction. The materials were mixed in a covered, but not sealed, ball flask at 130° C. in an oil bath for 24 hours. Ester bonds form in the reaction between PLGA and PEG while the byproduct of H2O was evaporated off during the reaction. The copolymer was then coupled by adding HMDI and was mixed in an oil bath at 60° C. for 12 hours. The final product was two PEG-PLGA diblocks coupled in the middle with HMDI to form a PEG-PLGA-HMDI-PLGA-PEG polymer chain. The chemical structure of the resulting polymer chain is shown in FIG. 2.

Because the HMDI coupler of the two PLGA chains is somewhat insignificant compared to the high molecular weight PLGA and PEG, the product is considered a triblock copolymer, PEG-PLGA-PEG, with a large PLGA chain between two PEG components. HMDI was added in a 0.5 molar equivalence to the mass of the PEG. A reflux was then performed at 110° C., the boiling temperature of toluene, for 12 hours. Afterward, the material was precipitated in cold diethyl ether, dissolved in dichloromethane (DCM), and then re-precipitated in cold diethyl ether to remove any impurities. Finally, the PEG-PLGA-PEG triblock copolymer was placed in a vacuum oven overnight to remove any residual solvents. The material was then stored at −20° C. to prevent any degradation of the PLGA.

Additional steps involving rotoevaporation were added later to help guarantee the absence of unwanted solvents, including toluene, diethyl ether, and dichloromethane. Rotoevaporating, or rotary evaporator, entails using a device to efficiently and gently remove solvents from samples by evaporation. The sample is places in a ball flask and rotated while in a hot bath of water or oil. The contents are put under vacuum to help assist in quickly evaporating any excess solvents. The rotary motion allows for more surface area for solvents to evaporate quicker. These two additional rotoevaporation steps were added after the reflux and after the copolymer was re-precipitated in dichloromethane. The rotoevaporation was conducted at 80° C. and under vacuum.

The synthesis of PEGma-PLGA-PEGma is almost identical to the synthesis of PEG-PLGA-PEG. Using PEG methacrylate (Mw=526), ring opening polymerization to form diblocks and coupling of the diblocks to form triblocks proceeded. The material was rotoevaporated under vacuum for 30 minutes in a water bath at 85° C. before being dissolved in dichloromethane and then precipitated in cold diethyl ether to remove any impurities. Again, the material was rotoevaporated and then was placed in a vacuum oven overnight to remove any residual solvents and finally stored at −20° C. to prevent degradation of the PLGA. The resulting PEGma-PLGA-PEGma has the formula shown in FIG. 5.

To prepare the triblock copolymer for printing, DI water was added and the solution was stirred at 4° C. for 24 hours with constant inspection to ensure homogeneity. The product was then characterized by spectroscopy and rheology to determine its molecular composition, viscosity, and elastic and viscous moduli.

Figures 5, 6:
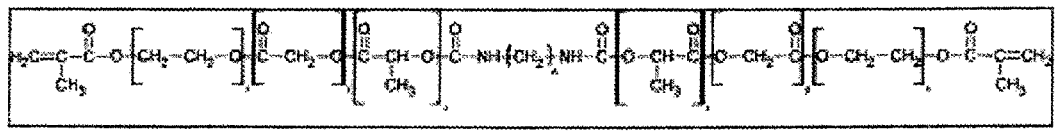
FIG. 5 shows the chemical formula of a PEGma-PLGA-PEGma triblock polymer.
FIG. 6 shows a table of viscosities, temperatures, and elastic moduli for various mix ratios of PEG-PLGA-PEG/PEGma-PLGA-PEGma.
Figure 7:
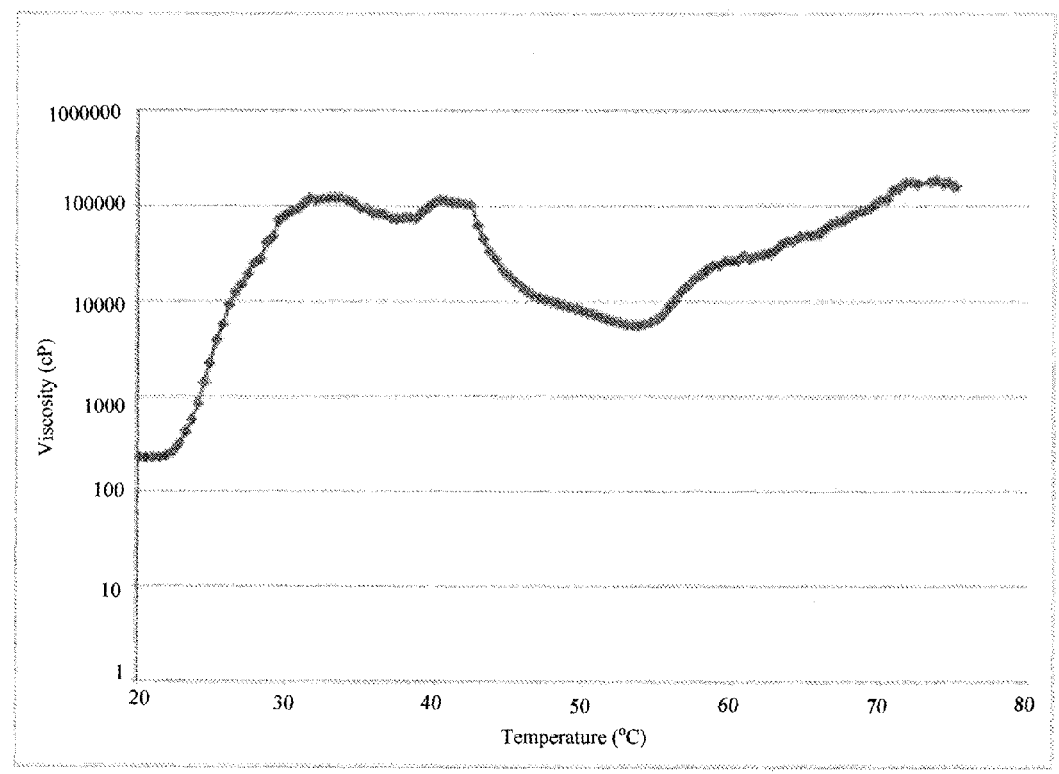
FIG. 7 shows a graph of Viscosity v. Temperature for a 20/80 blend of PEG-PLGA-PEG/PEGma-PLGA-PEGma.
Figure 8:
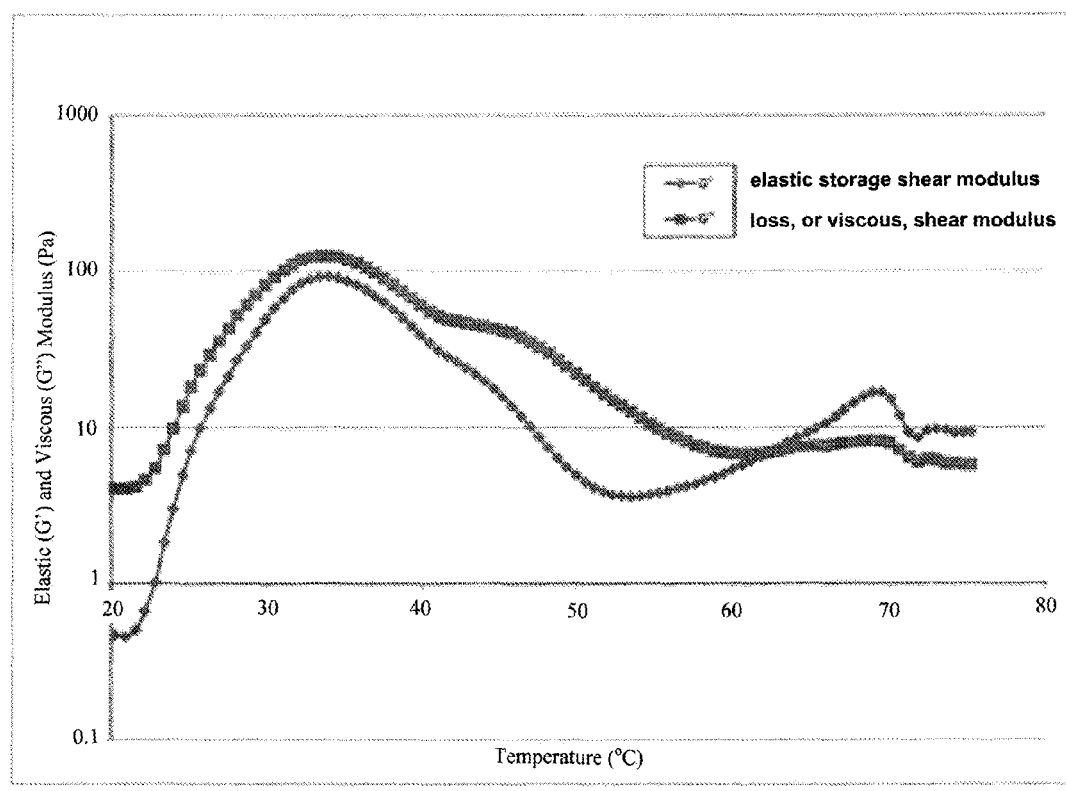
FIG. 8 shows a graph of elastic storage shear modulus and loss, or viscous, shear modulus v. Temperature for a 20/80 blend of PEG-PLGA-PEG/PEGma-PLGA-PEGma.

At a maximum viscosity of 122,836 cP, similar to sour cream and peanut butter, a 20/80 mix of PEG-PLGA-PEG and PEGma-PLGA-PEGma had the greatest viscosity of mix ratios of 50/50, 35/65, 20/80, and 10/90, as shown in FIG. 6. It also had the highest solution minimum viscosity of 228 cP, which is shown in FIG. 7. The 20/80 mix of material observed the closest maximum viscosity and maximum elastic modulus temperatures of 33.3° C. and 33.98° C. respectively. The material did not technically gel when the elastic modulus was at its maximum but as the temperature increased, elastic storage shear modulus did become greater than loss, or viscous, shear modulus, as shown in FIG. 8. High elastic and viscous moduli data and the increase in viscosity at extreme high temperature are due to some water evaporation during testing. This material was able to fully and irreversibly gel under UV light in less than 1 minute. It is possible to view a 3-D structure with the 20/80 gel due to the quick photoresponsiveness of the material.

Figure 9A:
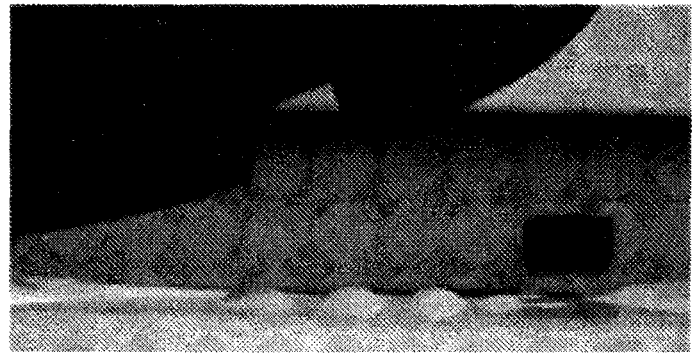
FIG. 9A shows a side elevation view of a plurality of drops of the PEG-PLGA-PEG/PEGma-PLGA-PEGma blend prior to ultraviolet irradiation.
Figure 9B:
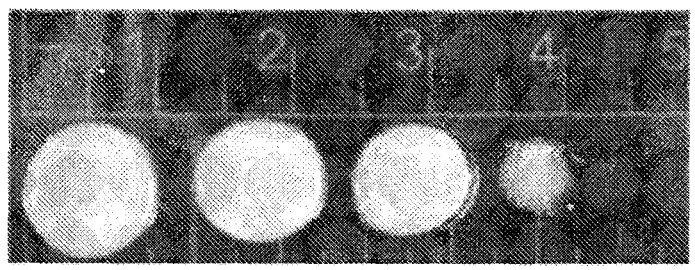
FIG. 9B shows a top plan view of the plurality of drops shown in FIG. 9A.
Figure 9C:
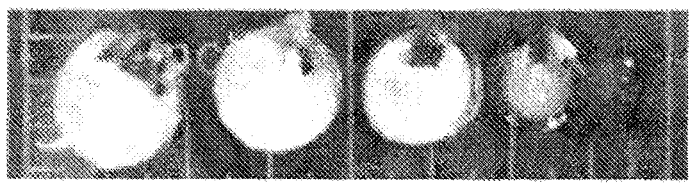
FIG. 9C shows a top plan view of the plurality of drops after ultraviolet irradiation.
Figure 9D:
FIG. 9D shows a side elevation view of the plurality of drops shown in FIG. 9C.

To further test the 3-D building ability of the 20/80 material, a row of droplets were pipetted onto a glass slide, as shown in FIGS. 9A and 9B. A series of droplets on top of the old droplets were repeated after gelation of the previous droplet. After 10 seconds of UV light irradiation for each round of droplets, another round of droplets was placed. As shown in the final gelation pictures of FIGS. 9C and 9D, the material is capable of holding its shape and building vertically. To also demonstrate the shape holding aspects of this material, some of the droplets were peeled back off of the glass slide (not shown).

An exemplary method of manufacturing the inventive material includes the steps of providing the first triblock polymer having the formula ABA, such as, for example, PEG-PGLA-PEG and blending the second triblock polymer having the formula AmaBAma, such as, for example, PEGma-PLGA-PEGma, with the first triblock polymer, forming a blend. The ratio of PEG-PLGA-PEG to PEGma-PLGA-PEGma is about 20/80 by weight. The two polymers are mixed in DI water to form a solution with about 0.03 percent by weight of a photoinitiator.

The blend can be used in a SFF printer for 3-D printing of scaffold material. The blend is heated as it is ejected from the printer to between about 33 degrees Celsius and about 34 degrees Celsius, raising the viscosity of the blend from less than about 230 cP to over about 122,000 cP and raising the maximum elastic modulus to over about 93 Pascals. The blended material is then irreversibly crosslinked by irradiating the blend with ultraviolet light. In an exemplary embodiment, the blend is irradiated with a 365 nanometer ultraviolet light after about 10 layers of the material are deposited onto a substrate (not shown).

Degradation is important in tissue engineering materials to allow for encapsulated cells and growth of surrounding tissue into the scaffold. Another advantage of degradation is to allow for drug delivery at the repaired site. The drug release of spironolactone in PBS was studied from a PEG-PLGA-PEG (550-2810-550) triblock material and was found to fully release after 58 days. The benefit of using a PEG-PLGA-PEG material is that the PLGA is biodegradeable, which permits the release of drugs and the growth of cells. The degradation rate of PLGA has been researched and found to depend on several factors including D,L-lactide-glycolide ("DLLA: GA") ratio, molecular weight, and water content.

Because the degradation rate of the PLGA is adjustable, based on these factors, the degradation rate of the inventive material can also be adjusted accordingly. Further, adjusting the ratio of PEG-PLGA-PEG/PEGma-PLGA-PEGma from 20/80 to other values also adjusts the degradation rate of the material.

It is desired that the inventive material degrade over time so that it can be replaced by live tissue growing through the scaffold.

The inventive material has an elastic modulus that is compatible with human soft tissue, such as, for example, the heart and liver, and can therefore be used as scaffold material in conjunction with such organs.

It will be further understood that various changes in the details, materials, and arrangements of the parts which have been described and illustrated in order to explain the nature of this invention may be made by those skilled in the art without departing from the scope of the invention as expressed in the following claims.

We claim:

1. A hydrogel material comprising:
   a first triblock polymer having a formula ABA; and
   a second triblock polymer having a formula AmaBAma, wherein:
   A is polyethylene glycol;
   B is poly(DL-lactic acid-co-glycolic acid); and
   Ama is a methacrylate of the first polymer, wherein the material is thermosensitive and photocrosslinkable.

2. The hydrogel material according to claim 1, wherein about 20 percent by weight of the blend comprises the first triblock polymer and about 80 percent by weight of the blend comprises the second triblock polymer.

3. A hydrogel material comprising:
   a first triblock polymer having a formula ABA; and
   a second triblock polymer having a formula AmaBAma, wherein:
   A is a first polymer;
   B is a second polymer; and
   Ama is a methacrylate of the first polymer, wherein the material is thermosensitive and photocrosslinkable and wherein A has a first molecular weight, and wherein B has a second molecular weight, about 5.1 times the first molecular weight.

4. The hydrogel material according to claim 1, wherein about 0.03 percent by weight of the blend comprises a photoinitiator.

5. The hydrogel material according to claim 1, wherein the material has a maximum viscosity of over about 122,000 centipoise at a temperature between about 33 degrees Celsius and about 34 degrees Celsius.

6. The hydrogel material according to claim 1, wherein the material has a maximum elastic modulus of over about 93 Pascals at a temperature between about 33 degrees Celsius and about 34 degrees Celsius.

7. The hydrogel material according to claim 1, wherein A is a hydrophilic material and wherein B is a hydrophobic material.

8. A method of manufacturing a polymer composite comprising the steps of:
   (a) providing a first triblock polymer having a formula ABA;
   (b) blending a second triblock polymer having a formula AmaBAma with the first triblock polymer, forming a blend,
   wherein:
      A is polyethylene glycol;
      B is poly(DL-lactic acid-co-glycolic acid); and
      Ama is a methacrylate of the first polymer; and
   (c) heating the blend to between about 33 degrees Celsius and about 34 degrees Celsius.

9. The method according to claim 8, further comprising providing about 0.03 percent by weight of a photoinitiator.

10. The method according to claim 8, wherein step (c) comprises raising the viscosity of the blend to over about 122,000 centipoise.

11. The method according to claim 8, wherein step (c) comprises raising the maximum elastic modulus to over about 93 Pascals.

12. The method according to claim 8, wherein, prior to step (c), the blend has a viscosity of less than about 230 centipoise.

13. The method according to claim 8, further comprising, after step (c), irradiating the blend with ultraviolet light.

14. The method according to claim 8, further comprising providing about 20 percent by weight of the first triblock polymer and about 80 percent by weight of the second triblock polymer for the blend.

15. The method according to claim 8, further comprising, prior to step (c), dissolving the blend in water.

* * * * *